US006391596B1

(12) United States Patent
Talashek et al.

(10) Patent No.: US 6,391,596 B1
(45) Date of Patent: May 21, 2002

(54) HIGH VISCOSITY XANTHAN AND PROCESS FOR PREPARING SAME

(75) Inventors: Todd A. Talashek; William Scott Bousman, both of San Diego, CA (US)

(73) Assignee: CP Kelco U.S., Inc., Wilmington, DE (US)

( * ) Notice: Subject to any disclaimer, the term of this patent is extended or adjusted under 35 U.S.C. 154(b) by 0 days.

(21) Appl. No.: 09/665,542

(22) Filed: Sep. 19, 2000

Related U.S. Application Data

(63) Continuation of application No. 08/936,576, filed on Sep. 25, 1997, now abandoned.

(51) Int. Cl.[7] .......................... C12P 19/06; C08B 37/00

(52) U.S. Cl. ......................... 435/104; 435/101; 422/26; 426/521; 536/114; 536/123

(58) Field of Search ................................ 435/101, 104; 422/26; 426/521;

(58) Field of Search ................................ 536/114, 123

(56) References Cited

U.S. PATENT DOCUMENTS

| 3,355,447 | A | * | 11/1967 | O'Connell | 435/104 |
|---|---|---|---|---|---|
| 3,773,752 | A | * | 11/1973 | Buchanan | 435/104 |
| 4,094,739 | A | * | 6/1978 | Schroeck | 435/104 |
| 4,299,825 | A | * | 11/1981 | Lee | 424/180 |
| 5,413,804 | A | * | 5/1995 | Rhodes | 426/583 |

* cited by examiner

*Primary Examiner*—Francisco Prats
(74) *Attorney, Agent, or Firm*—Fitzpatrick, Cella, Harper & Scinto (57) ABSTRACT

The present invention is related a high viscosity xanthan and processes for producing said high viscosity xanthan. In particular, the invention relates to a process for increasing the viscosity of xanthan comprising the steps of: (i) diluting xanthan in a fermentation broth with more than 30 percent by volume of a diluent to said fermentation broth volume; and (ii) pasteurizing said diluted xanthan fermentation broth. A particularly preferred pasteurization process is to utilize steam from a direct steam injection system. Xanthans with increased viscosities have improved product functionality for a number of different commercial applications are produced using the processes of the present invention.

24 Claims, 2 Drawing Sheets

HIGH VISCOSITY XANTHAN AND PROCESS FOR PREPARING SAME

This application is a continuation of Ser. No. 08/936,576 filed Sep. 25, 1997, now abandoned.

BACKGROUND OF THE INVENTION

1. Field of the Invention

This invention relates to a high viscosity xanthan and processes for the preparation of the high viscosity xanthan. One preferred embodiment is directed to dilution of a xanthan fermentation broth (solution) to produce a high viscosity xanthan. In another preferred embodiment pasteurization of a xanthan fermentation broth (solution) by a direct steam injection system provides a xanthan having increased viscosity compared to its native form. This invention is further related to a high viscosity xanthan produced by the processes of this invention.

2. Related Background Art

The fermentation of carbohydrates to produce the biosynthetic water-soluble polysaccharide xanthan gum by the action of Xanthomonas bacteria is well known. The earliest work was conducted by the United States Department of Agriculture and is described in U.S. Pat. No. 3,000,790. Xanthomonas hydrophilic colloid ("xanthan") is an exocellular heteropolysaccharide. The heteropolysaccharide has a backbone chain of (1→4)-β-glucose residues substituted by short, lateral chains linked to alternate monomeric residues of the main chain (Milas and Rinaudo, Carbohydrate Research, 76, 189–196, 1979). Xanthan has a wide variety of industrial applications including use in oil well drilling muds, as a viscosity control additive in secondary recovery of petroleum by water flooding, as a thickener in foods, as a stabilizing agent, and as a emulsifying, suspending and sizing agent (Encyclopedia of Polymer Science and Engineering, 2nd Edition, Editors John Wiley & Sons, 901–918, 1989). Xanthan can also be used in cosmetic preparations, pharmaceutical vehicles and similar compositions.

Xanthan is produced by aerobic submerged fermentation of a bacterium of the genus Xanthomonas. The fermentation medium contains carbohydrate (such as sugar), trace elements and other nutrients. Once fermentation is complete, the resulting fermentation broth (solution) is heat-treated. It is well established that heat treatment of xanthan fermentation broths and solutions leads to a conformational change of native xanthan at or above a transition temperature ("$T_m$") to produce a higher viscosity xanthan. Heat treatment also has the beneficial effect of destroying viable microorganisms and undesired enzyme activities in the xanthan. Following heat-treatment, the xanthan is recovered by alcohol precipitation. However, heat treatment of xanthan fermentation broths (solutions) also has disadvantages, such as thermal degradation of the xanthan. Heating xanthan solutions or broths beyond $T_m$ or holding them at temperatures above $T_m$ for more than a few seconds leads to thermal degradation of the xanthan. Degradation of xanthan irreversibly reduces its viscosity. Accordingly, heat treatment is an important technique with which to control the quality and consistency of xanthan.

Xanthan quality is primarily determined by two viscosity tests that are well known to those skilled in the art, i.e., the Low Shear Rate Viscosity ("LSRV") in tap water solutions and the Sea Water Viscosity ("SWV") in high salt solutions. Pasteurization of xanthan fermentation broths at temperatures at or above $T_m$ have been found to result in the recovered xanthan having a higher viscosity as indicated by higher LSRV and SWV values.

The processes occurring during thermal treatment of xanthan fermentation broth (solution) are not well understood. It is believed that two processes occur during the thermal treatment of xanthan fermentation broth. Firstly, the thermal heating induces a conformation change which unwinds the double stranded native xanthan into a disordered xanthan which on cooling renatures to form an ordered xanthan. The renatured ordered xanthan has a higher viscosity compared to the native ordered xanthan which has not been pasteurized. Secondly, a competing degradation process may occur during the pasteurization (heat-treatment) which cleaves the native xanthan strands into shorter pieces resulting in a substantial decrease in viscosity. Studies have shown that the processes resulting in the desired conformational change occur rapidly, on the order of seconds, once $T_m$ is reached (Norton et al., Journal of Molecular Biology, 175, 371–394, 1984). Conversely, the thermal degradation process is slow, on the order of minutes at typical operating temperatures, but accelerates with increasing temperature. Below a temperature of 70° C., thermal degradation appears to be negligible. Maximum xanthan viscosity is achieved by rapidly heating the xanthan broth at or above $T_m$ followed by rapid cooling. It is generally important to minimize the time that the fermentation broth temperature exceeds 70° C. in order to preserve the integrity of the final xanthan.

The relative viscosity at 25° C. of both native unpasteurized xanthan solutions and solutions which were previously pasteurized at various temperatures have been measured (Milas and Rinaudo, Polymer Bulletin, 12, 507–514, 1984). For solutions previously heated well above their $T_m$, a greater than three fold increase in the relative viscosity of the xanthan was observed. For solutions previously heated to temperatures near their $T_m$, partial increases in the relative viscosity, reflecting the fraction of molecules undergoing the conformational transition as determined from optical rotation measurements, were observed. These viscosity results, in addition to the observed hysteresis of the optical rotation curve upon an initial heating and cooling cycle of a xanthan solution, are consistent with the following model:

A maximum viscosity will be obtained when all xanthan molecules have been transformed from the native to the renatured conformation. However, if $T_m$ is high ($\geq 100°$ C.), pasteurization of the xanthan broth above $T_m$ can result in degradation of the xanthan molecules and a resulting decrease in product viscosity (lower LSRV and SWV values).

One of the variables $T_m$ depends upon is the ionic strength of the fermentation solution. The $T_m$ of aqueous xanthan solutions as a function of added sodium chloride has been measured (Milas and Rinaudo, Carbohydrate Research, 76, 189–196, 1979). The $T_m$ was found to vary linearly with the log of the total ionic strength (the ionic strength contains contributions from both the added sodium chloride and the xanthan molecules). The $T_m$ of xanthan has also been monitored in aqueous potassium chloride solutions using differential scanning calorimetry (Norton et al., Journal of Molecular Biology, 175, 371–394, 1984). A linear dependence of $T_m$ on the log of the ionic strength was also found.

A problem that has been identified with current recovery processes used to produce xanthan is the difficulty in achieving uniform heating of the broth. In particular, during pasteurization of the fermentation broth (solution) it is difficult to heat the broth in a uniform, controlled manner. As a result, some variability in the viscosity of xanthan recovered at the completion of the process may be observed. This may also give rise to reproducibility problems for xanthans having certain desired characteristics. Heating in a uniform and controlled manner is also dependent in part on the characteristics of the solution being heated. For example, xanthan fermentation broths are very viscous yet pseudo-plastic (shear-thinning). When high concentration xanthan solutions are heated in conventional heat exchangers, non-uniform heating will occur. It is difficult to achieve a uniform temperature and residence time for every element of fluid passing through conventional heat exchange equipment during pasteurization of xanthan. Thus, during the heating of a xanthan fermentor broth, the conductive and convective heat transfer are poor and the formation of unwanted temperature gradients in the broth are difficult to prevent. This results in xanthan viscosities far below what is theoretically achievable. For example, this occurs in a xanthan solution passing through a heated tube. Because of the high viscosity of xanthan solutions, turbulent mixing (the primary mechanism of heat transfer in non-viscous liquids passing over a heated surface) in a heated tube is minimal and heat transfer occurs primarily by a much slower conduction mechanism. In addition, the layers of fluid near the wall of the tube experience a higher shearing force and are thus less viscous than the layers in the center. This causes the center core of fluid to behave as a plug and reduces mixing with the higher temperature outer layers. In order for heat transfer to occur, the surface temperature of the tube wall must be greater than the desired average temperature of the xanthan solution. With poor mixing of the fluid, the outer layers of fluid tend to be overheated while layers in the center are under-heated. When these heat exchangers are dismantled for cleaning, the inside walls of the heated tubes are heavily coated with burned xanthan.

The poor fluid mixing in conventional heat transfer equipment also significantly reduces the efficiency of heat transfer, necessitating the use of very large surface area (large volume) heat exchangers. The use of large volume heat exchangers cause the xanthan solutions to remain at elevated temperatures long enough for thermal degradation of the polymer to begin, thus reducing the maximum viscosity achievable. In addition, the large mass of fluid and metal present in this type of equipment leads to poor automated process control because there is a time lag between changes in the input of the heating medium (usually steam) and the temperature response in the xanthan solution being heated. The result is a varying output temperature in the xanthan solution and sluggish response to temperature changes even when computer control is used.

Conventional production sized heat exchangers also suffer from another problem when processing highly pseudo-plastic fluids like xanthan. To increase the surface area available for heat transfer in a heat exchanger, many heated tubes or slots are placed in parallel with each other so that the fluid is divided into many smaller streams. The alternative would be to use a single channel of impracticably long length. Each channel will have a slightly different cross sectional area, leading to differing amounts of shear in each channel. Because xanthan is highly shear thinning, the result is uneven amounts of flow in different channels, leading again to uneven heating.

The problems described above lead to non-uniform heat treatment of the xanthan solution. This results in less than optimum development of xanthan viscosity, thermal degradation of the xanthan, incomplete destruction of unwanted enzymes and poor process control. A more effective process of heating xanthan solutions at or above $T_m$ for viscosity enhancement that will reduce loss of xanthan viscosity due to degradation from overheating of the xanthan solution or broth would be highly desirable. Furthermore, it would also be highly desirable to provide for processes that enhance the viscosity characteristics of xanthan while overcoming the current limitations encountered in the preparation of xanthan from fermentation broths (solutions). Xanthans that have been prepared by dilution of the fermentation broth with 25 percent or less of a diluent have been commercially available. Such xanthans have been pasteurized by steam injection have also been available. However, xanthans having improved viscosities over xanthans prepared in the above-described manner would be highly desirable. This invention provides a number of effective processes for enhancing the viscosity of xanthan, in addition to providing a process in which xanthan can be heated in a more uniform manner while attaining the desired characteristic of high viscosity.

SUMMARY OF THE INVENTION

This invention relates to a high viscosity xanthan and processes for producing said high viscosity xanthan compared to its unpasteurized native xanthan form.

One aspect of this invention is related to a process for increasing the viscosity of xanthan comprising the steps of: (i) diluting xanthan in a fermentation broth with more than 30 percent by volume of a diluent to said fermentation broth volume; and (ii) pasteurizing said diluted xanthan fermentation broth. A particularly preferred pasteurization process is to utilize steam from a direct steam injection system.

More specifically, the invention relates to a process for increasing viscosity of a xanthan comprising the following steps:

(i) producing said xanthan in a fermentation broth by aerobic fermentation of a bacterium:

(ii) diluting said xanthan in said fermentation broth with more than 30 percent by volume of a diluent to said fermentation broth volume;

(iii) pasteurizing said diluted xanthan using steam from a direct steam injection system;

(iv) cooling said pasteurized fermentation broth to an ambient temperature; and (v) precipitating said xanthan having an increased viscosity.

Yet another embodiment of this invention is directed to high viscosity xanthan prepared by the above-described processes. Xanthans with increased viscosities have improved product functionality for a number of different commercial applications are produced using the processes of the present invention.

BRIEF DESCRIPTION OF THE DRAWINGS

In describing the overall invention, reference will be made to the accompanying drawings, wherein.

DETAILED DESCRIPTION OF THE INVENTION

The term "xanthan" as used herein means the extracellularly produced biogum made by the heteropolysaccharide-producing bacterium of the genus Xanthomonas by the whole culture fermentation, under a variety of conditions, of a medium comprising: a fermentable carbohydrate, a nitrogen source, and other appropriate nutrients well known to those skilled in the art.

The present invention is related to a process for increasing the viscosity of xanthan comprising the steps of: (i) diluting xanthan in a fermentation broth with more than 30 percent by volume of a diluent to said fermentation broth volume; and (ii) pasteurizing said diluted xanthan fermentation broth to increase the viscosity of said xanthan. In one preferred embodiment, the invention relates to a process for increasing the viscosity of xanthan by pasteurizing a xanthan fermentation broth using steam from a direct steam injection system. Preferably, xanthan is diluted in the fermentation broth in which it was originally prepared, although it may be possible to reduce the volume of fermentation broth prior to dilution.

A preferred starting material for use in the process of the present invention is a Xanthomonas hydrophilic colloid solution prepared by the bacterium *Xanthomonas campestris*. While *Xanthomonas campestris* is the preferred bacterium, nevertheless related species of Xanthomonas also elaborate a hydrophilic colloid may be utilized. Such other species are, for example, *Xanthomonas begoniae, Xanthomonas malvaceraum, Xanthomonas carotae, Xanthomonas incanae, Xanthomonas phaseoli, Xanthomonas vesicatoria, Xanthomonas papavericola, Xanthomonas translucens, Xanthomonas vesicatoria,* and *Xanthomonas hedrae*.

The present invention also relates to a process for a high viscosity xanthan prepared by the process comprising the steps of: (i) producing a xanthan in a fermentation broth by aerobic fermentation of a bacterium; (ii) diluting said xanthan in said fermentation broth with more than 30 percent by volume of a diluent to said fermentation broth volume; and (iii) pasteurizing said diluted xanthan using steam from a direct steam injection system to form the high viscosity xanthan.

A particularly preferred embodiment of this invention is directed to a process for increasing viscosity of a xanthan comprising:

(i) producing said xanthan in a fermentation broth by aerobic fermentation of a bacterium:

(ii) diluting said xanthan in said fermentation broth with more than 30 percent by volume of a diluent to said fermentation broth volume;

(iii) pasteurizing said diluted xanthan using steam from a direct steam injection system;

(iv) cooling said pasteurized fermentation broth to an ambient temperature; and (v) precipitating said xanthan having an increased viscosity.

The diluent is generally water. Typically, the diluent is selected from the group consisting of deionized water, soft water and hard water. The fermentation broth is preferably diluted with more than 30 percent by volume of the diluent to the fermentation broth volume. More preferably, the fermentation broth is diluted with more than 50 by volume of the diluent to the fermentation broth volume. Most preferably, the fermentation broth is diluted with more than 100 percent by volume of the diluent to the fermentation broth volume. The biogum is generally precipitated with an alcohol, a ketone or any other miscible organic solvent. Preferably, the alcohol is methanol, ethanol, propanol, isopropanol (isopropyl alcohol) or butanol. Preferably, the ketone is acetone.

Preferably, the step of pasteurizing is conducted at a temperature from about 70° C. to about 120° C. for about 0.1 to about 5 minutes and more preferably from about 80° C. to about 110° C. for about 0.1 to about 5 minutes.

In the present invention steam is used to facilitate uniform heating of fermentation broths (solutions). Steam contains a large amount of energy per unit volume and is completely condensable into xanthan broths. As the steam condenses into the broth, the energy is released instantaneously, producing a sharp temperature increase. If steam were injected into a flowing stream of xanthan broth, it would mix poorly due to the lack of turbulent mixing processes in the broth and a two-phase steam-broth mixture would likely result. In addition to flow rate control problems, this would result in uneven heating of the broth and a wide variation in viscosity would be expected. If however, the steam and broth are combined in a high intensity mixing zone, the condensation of the steam should be instantaneous and a single phase broth (diluted by the steam) results. If a high energy (high pressure) steam source is used, dilution of the product by the steam condensate can be minimized and thus the dilution rate of the fermentation broth controlled. The pasteurization temperature may be adjusted by controlling the amount of steam injected into the system. The uniform pasteurized mixture is then passed through a cooler to reduce the temperature quickly after the steam injection. The steam injection step in combination with the dilution step of this invention has been found to significantly improve the viscosity of the resulting xanthan as compared to the existing prior art processes used to prepare xanthan.

Mixing after steam injection is important so as to uniformly heat the broth to a temperature which is determined by the proportions of steam and broth present. The surface area for heat transfer at the surface of numerous small steam bubbles is extremely large and the need for parallel heating tubes as in the prior art is eliminated. Thus all the broth passes through a single homogeneous, high temperature zone leading to precise temperature and residence time control. Because the heating zone can be made to have a very small volume, computerized process control of the broth temperature is possible as the controller can easily monitor and detect changes in the system.

The steam injection process also may provide the additional benefit that more complete destruction of unwanted enzymes is likely to occur when heating is accomplished using the process of this invention.

Finally, maintenance costs are substantially reduced by using direct steam injection heating instead of steam heated exchangers because burned biogum product is not produced. This is in contrast to the plate and frame heat exchangers which must be rebuilt semi-annually due to build up of burned biogum on the heated surfaces. The reduction in maintenance makes the dilution/steam injection process of this invention a very cost effective process to reduce long term production costs and eliminate down-time during rebuilding of plate and frame heat exchanger systems.

It has been found that dilution with water, particularly, deionized water, tap water or soft water, followed by pasteurization by steam injection results in an increase in the viscosity of recovered xanthan compared to its native form. Dilution with deionized water has been found to give the highest LSRV and SWV for a xanthan, while giving the lowest ionic strength for the fermentation broth (solution) as measured by conductivity.

It is known that $T_m$ linearly depends on the log of the total ionic strength of the fermentation broth. Accordingly, dilution of the fermentation broth results in a decrease in $T_m$ which allows for pasteurization of the fermentation broth at a lower $T_m$ compared to pasteurization of the broth in the absence of dilution. Without being bound by theory, it is believed that when a diluted xanthan broth is heated to its $T_m$ the xanthan molecules are transformed to a renatured, ordered xanthan upon cooling. This renatured, ordered xanthan has a higher viscosity than native xanthan. Therefore, by diluting with sufficient levels of deionized water $T_m$ can be reduced to temperatures where thermal degradation of the xanthan molecules is minimized, thus resulting in products having significantly higher viscosities than are achievable without dilution.

Again, without being bound to theory, it is believed that the high product viscosities (LSRV and SWV) obtained by xanthan broth dilution with deionized water is due to the efficient lowering of the $T_m$ prior to pasteurization. It has been found that reduction in the ionic strength by the fermentation broth, prior to pasteurization, by other techniques such as ultrafiltration or diafiltration are not as effective as addition of a diluent in maximizing product viscosities. It is believed that contributions to the ionic strength of the fermentation broth come from the xanthan molecules and their counterions in addition to the residual salts. It is further believed that ultrafiltration and diafiltration are not as effective as dilution in lowering ionic strength because these techniques only lower the concentration of the residual salts and not the xanthan molecules.

Xanthan having improved viscosities prepared by the process of this invention results in improved product functionality in a number of different applications. An increase in viscosity at low shear rate is associated with an improved suspending and stabilizing abilities. For example, a xanthan having a higher SWV is very beneficial in oil field drilling applications. Xanthan may be a component of the drilling fluid in an oil field and an increase in xanthan viscosity will enhance the drilling fluid's ability to suspend and therefore remove cuttings as the drilling of the oil well proceeds. In food applications, such as salad dressings, an increase in the xanthan viscosity will increase the stability of the oil in water emulsion (preventing separation), thus extending the shelf-life of the dressing.

As described previously, a preferred process of the present invention employs a direct steam injection system to introduce the hot steam into a diluted xanthan fermentation broth to pasteurize the broth. A xanthan having a higher viscosity compared to native xanthan or xanthan produced using dilution without direct steam injection pasteurization is obtained.

The high viscosity xanthans of the present invention preferably have a sea water viscosity greater than 25 dial reading ("D.R."), more preferably a sea water viscosity greater than 30 D.R. and most preferably a sea water viscosity greater than 35 D.R. Dial readings are determined at 3 revolutions per minute using a Fann 35 viscometer equipped with a 0.2 spring (Fann Instrument Corp., Houston, Tex.). The xanthans of the present invention preferably have a low shear rate viscosity greater than 2000 cP, more preferably greater than 3000 cP and most preferably greater than 3500 cP at 3 revolutions per minute as measured on a Brookfield Model LV viscometer equipped with a No. 2 spindle (Brookfield Engineering Laboratories, Inc., Stoughton, Mass.).

Figure 1:
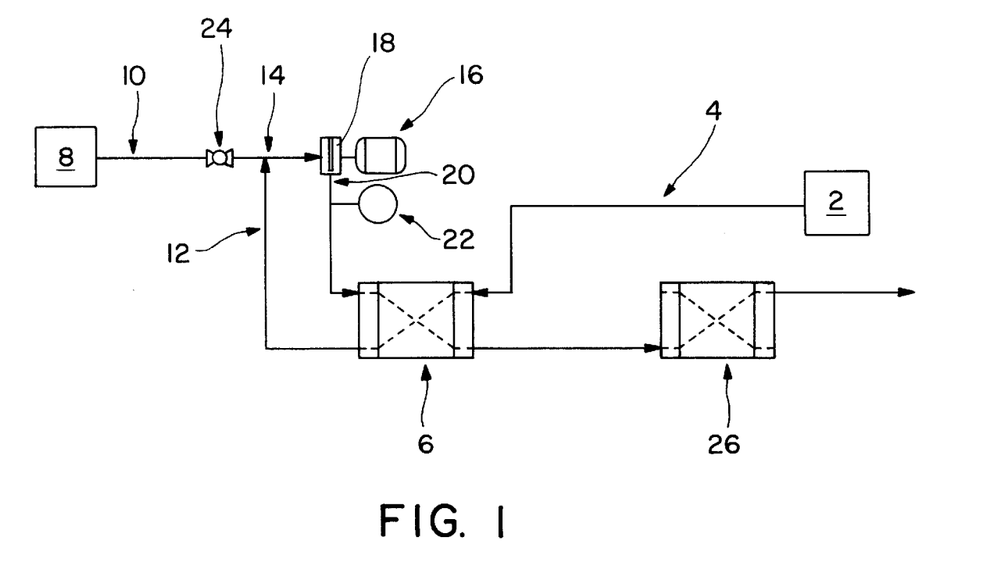
FIG. 1 shows a schematic of a process for direct steam injection pasteurization of a fermentation broth (solution) using a direct steam injection system having an in-line mixer.

Referring now to the drawings, one preferred embodiment for the preparation of high viscosity xanthan using the process of the present invention employs an in-line mixer as illustrated in FIG. 1. After dilution, xanthan broth 2 is fed in a tube 4 through a plate heat exchanger regeneration section 6 where the broth is heated to a desired temperature prior to contact with steam. Steam 8 is injected through a tube 10 and contacts the broth fed through a tube 12 at the inlet area 14 of an in-line mixer 16, e.g., a Silverson Machines Model 275 L in-line mixer (Silverson Machines, East Longmeadow, Mass.). An impeller 18 mixes the steam and xanthan broth to form a single phase mixture. In the in-line mixer, the steam is mixed into very small bubbles into the broth which condense and transfer latent and sensible heat to the broth. The enthalpy of the steam is approximately ten times that of the xanthan broth at the desired temperature so the broth is diluted by about 10 volume percent. The single phase heated broth mixture with no discrete steam bubbles passes out of the in-line mixer through an outlet tube 20 and temperature and pressure measurements are made using a gauge 22 near the outlet tube. The temperature of the system is adjusted with a valve 24 on the steam supply. The xanthan passes through the plate heat exchanger regeneration section 6 and then through an plate heat exchanger cooling section 26 prior to recovery.

Figure 2:
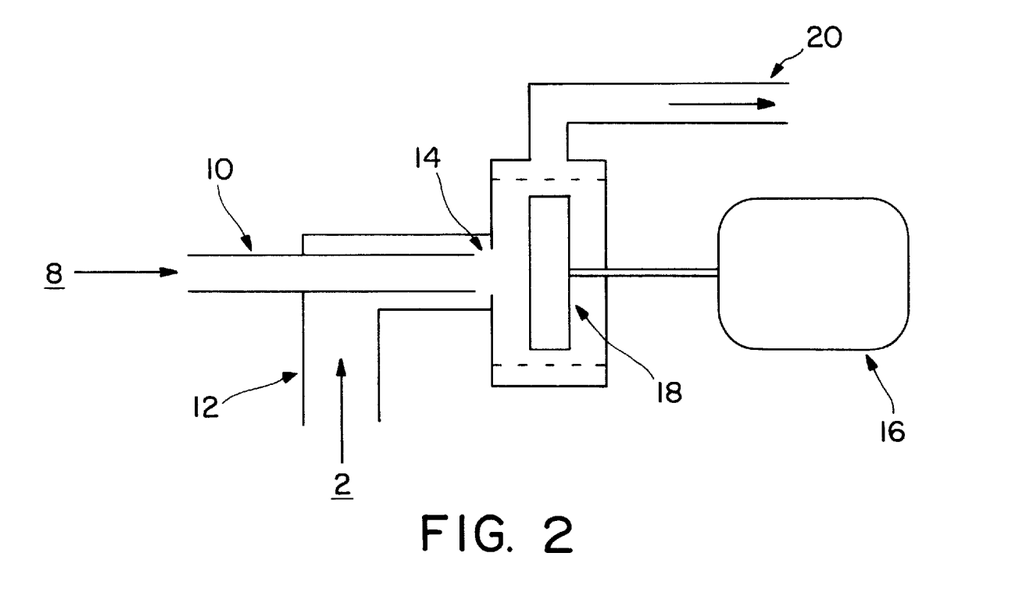
FIG. 2 shows an expanded view of the in-line mixing area of the direct steam injection system of FIG. 1.

FIG. 2 is an enlarged view of the in-line mixing area of FIG. 1. Steam 8 is injected through a tube 10 which contacts broth 2 fed through tube 12 at the inlet area 14 of the in-line mixer 16. The impeller 18 mixes the steam and xanthan broth to form a single phase mixture which exits through the outlet tube 20.

Figure 3:
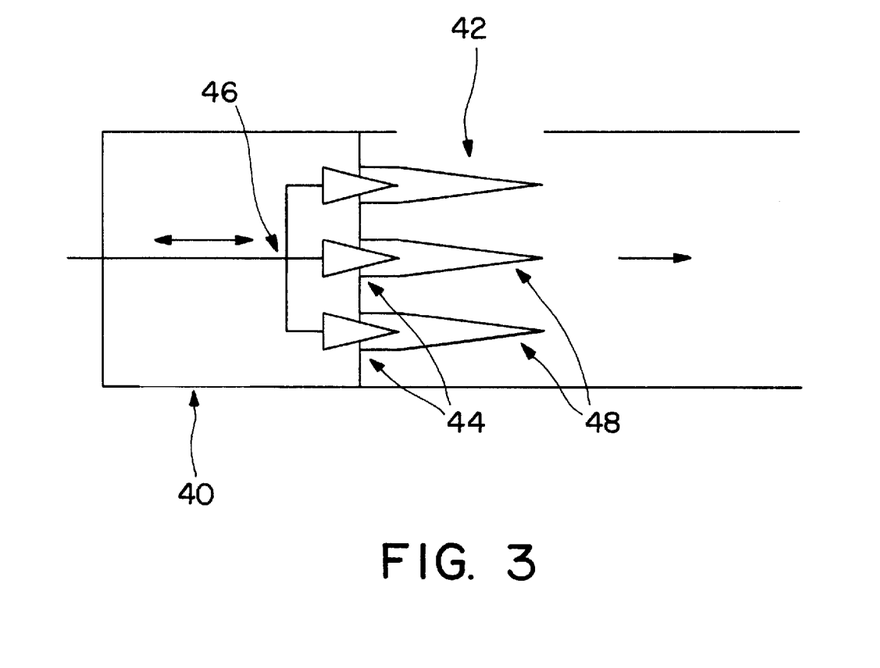
FIG. 3 shows an expanded view of a direct steam injection system using a QJet Heater (QJet Systems Inc., Lewiston, N.Y.) for pasteurization of a fermentation broth.

A particularly preferred process for direct steam injection pasteurization of a fermentation broth (solution) is a QJet Heater. FIG. 3 shows the mixing area of a direct steam injection system for the preparation of a high viscosity xanthan. Steam 40 is metered into the fermentation broth 42 through a set of variable area orifices 44 which are open and closed by an actuator shaft 46. As the steam contacts the fermentation broth, it forms condensing steam jets 48 with intense mixing of the fermentation broth and steam occurring. The QJet heater has few moving parts and no mechanical seals and thus has improved reliability compared to a traditional in-line mixer.

The temperature of the above-described system may be regulated manually or automatically and is very precise due to the small volume and short residence time in the in-line mixer. The use of an automated temperature control has the added benefit that the response to temperature changes is nearly instantaneous. The temperature range that the QJet heater can operate in can be shifted with changes in the steam supply pressure or changes in the diameter of the holes in the QJet heater orifice plate.

This invention will be better understood from the Examples which follow. However, one skilled in the art will readily appreciate that the specific methods and results discussed are merely illustrative of the invention and no limitation of the invention is implied.

Xanthomonas Fermentation Broth

Preparation of xanthan fermentation broths (solutions) are well known in the art. For example, as described in U.S. Pat. Nos. 4,758,356, 5,194,396, 3,232,929, 3,338,792 and 4,868, 293, the disclosures of which are hereby incorporated by reference herein.

EXAMPLE 1
Determination of Low Shear Rate Viscosity ("LSRV") for Xanthan

Low Shear Rate Viscosity for xanthan was determined using the following procedure. Xanthan (0.75 gm-weighed to the nearest 0.01 gm) was slowly added to 299 ml of synthetic tap water contained in a 400 ml Berzelius (tall form) beaker while stirring at 800±20 rpm. Stirring was continued for approximately 4 hours. Just before removing the test solution from stirring (after 4 hours), the solution temperature was adjusted to 25±2° C. The test solution was removed from the stirrer and allow to sit undisturbed at room temperature for 30±5 minutes (may be placed in a temperature-controlled water bath). After the solution sat for 30 minutes, the temperature was measured by inserting a thermometer into the solution between the center and the side of the beaker. It is important not to disturb the solution prior to measuring the viscosity. The viscosity at 25±2° C. was measured using a Brookfield Model LV Viscometer at 3 rpm using a No. 1 Spindle. Note that if solution temperature is out of range (25±2° C.), the solution was discarded and a new test solution was prepared. Note that if the viscosity is out of range, a No. 2 spindle is used for the viscosity determination. The viscosity in centipoise ("cP") was recorded after allowing the spindle to rotate for 3 minutes.

EXAMPLE 2
Determination of Sea Water Viscosity ("SWV") for Xanthan

Sea Water Viscosity for xanthan was determined using the following procedure. 300 mls of sea water solution, taken from a one liter stock solution made up of 41.953 g of sea salt (ASTM D-1141-52) in deionized water, was transferred to a mixing cup that was attached to a Hamilton-Beach 936-2 mixer (Hamilton-Beach Div., Washington, D.C.) and a single fluted disk was attached to the mixing shaft. The mixer shaft was initially rotated at approximately 4,000–6,000 rpm. 0.86 gm of xanthan was slowly added over 15–30 seconds to the mixing cup and allowed to mix for 5 minutes.

The mixer was set to 11,000±1,000 rpm and the test solution was allowed to mix for approximately 40 minutes. The mixture was allowed to mix for a total of 45 minutes, starting from time of xanthan addition. At the end of the 45 minutes mixing time, 2–3 drops of Bara Defoam (NL Baroid/NL industries, Inc., Houston, Tex.) was added and stirring was continued for an additional 30 seconds.

The mixing cup was removed from the mixer and immersed in chilled water to lower the fluid's temperature to 25±0.5° C. In order to insure a homogeneous solution, the solution was re-mixed after cooling for 5 seconds at 11,000±1,000 rpm. The solution was transferred from the mixing cup to 400 ml pyrex beaker and Fann viscosity (Fann Viscometer, Model 35A) was measured. This was accomplished by mixing at low speed (about 3 rpm). The reading was allowed to stabilize and then the shear stress value was read from the dial and recorded as the SWV dial reading at 3 rpm.

EXAMPLE 3
Preparation of High Viscosity Xanthan Using Dilution of Xanthan Broths Prior To Pasteurization Aliquots of a xanthan fermentation broth were diluted with various amounts of deionized water in the ratios shown in Table 3-1. Two of the aliquots were not diluted and were used as controls. Two of the diluted aliquot broths and one undiluted aliquot control were heated to 92° C. by passing the diluted broths through a heated coil and held at 92° C. for 5 minutes before cooling to ambient temperature and were then precipitated with 2.5 volumes of isopropyl alcohol. The remaining three aliquots (two diluted and one undiluted) were kept at ambient temperature and then xanthan was precipitated from each of the aliquots with 2.5 volumes of isopropyl alcohol. The recovered xanthan fibers were dried and milled into a powdered form.

The powdered xanthan samples were rehydrated in synthetic tap water (1000 ppm NaCl and 147 ppm $CaCl_2 \cdot 2H_2O$) and seawater at xanthan concentrations of 0.25% and 0.29%, respectively. The LSRV for each of the xanthans were measured as described in Example 2. The SWV for each of the xanthans was measured as described in Example 3. The LSRV and SWV results are set forth in Table 3-1.

TABLE 3-1

Dilution ratios for water:xanthan broth, pasteurization temperatures and LSRV and SWV results.

| Dilution Ratio (water:broth) | Heating Temp. (° C.) | LSRV (cP) | SWV (D. R.) |
|---|---|---|---|
| 0:1 | none | 414 | 13.5 |
| 2:1 | none | 478 | 14.5 |
| 3:1 | none | 518 | 16.0 |
| 0:1 | 92 | 1226 | 20.0 |
| 2:1 | 92 | 1596 | 23.0 |
| 3:1 | 92 | 2910 | 28.0 |

EXAMPLE 4
Preparation of High Viscosity Xanthan Using Dilution of Xanthan Broths Prior To Pasteurization Aliquots of a xanthan fermentation broth were diluted with various amounts of deionized water in the ratios shown in Table 4-1. The diluted broths were pasteurized by pumping the broths through a heated coil at 90° C. for 5 minutes, then cooled and the xanthan present in each sample was then precipitated with 2.5 volumes of isopropyl alcohol. The recovered xanthan fibers were dried and milled into a powdered form. The recovered powders were rehydrated in synthetic tap water and seawater as in Example 3. The LSRV and SWV were measured as described in Examples 1 and 2, respectively and the results are set forth in Table 4-1.

TABLE 4-1

Dilution ratios for water:xanthan broth, pasteurization temperatures and LSRV and SWV results.

| Dilution Ratio (water:broth) | Heating Temp. (° C.) | LSRV (cP) | SWV (D. R.) |
|---|---|---|---|
| 0:1 | none | 605 | 15.0 |
| 0:1 | 90 | 1060 | 17.0 |
| 1:5 | 90 | 1200 | 19.0 |
| 1:4 | 90 | 1220 | 18.0 |
| 1:3 | 90 | 1310 | 19.0 |
| 1:2 | 90 | 1300 | 20.0 |
| 1:1 | 90 | 1570 | 21.0 |

EXAMPLE 5
Preparation of High Viscosity Xanthan Using Dilution of Xanthan Broths Prior To Pasteurization A xanthan fermentation broth was divided into aliquots, which were diluted with deionized water in the ratios shown in Table 5-1, prior to pasteurization. The diluted broths were pasteurized by passing the broths through heated tubes at temperatures shown in Table 5-1 for 5 minutes, then cooled and precipitated with 2.5 volumes of isopropyl alcohol. The recovered xanthan fibers were dried and milled into a powdered form. The recovered xanthan powders were rehydrated in synthetic tap water and seawater as in Example 3. The LSRV and SWV were measured as described in Examples 1 and 2, respectively and the results are presented in Table 5-1.

TABLE 5-1

Dilution ratios for water:xanthan broth, pasteurization temperatures and LSRV and SWV results.

| Dilution Ratio (water:broth) | Heating Temp. (° C.) | LSRV (cP) | SWV (D. R.) |
|---|---|---|---|
| 0:1 | 100 | 1170 | 19 |
| 1:1 | 100 | 2000 | 24 |
| 3:1 | 100 | 2020 | 27 |
| 5:1 | 70 | 2320 | 27 |
| 5:1 | 80 | 2500 | 28 |
| 5:1 | 90 | 2000 | 25 |
| 7:1 | 70 | 2450 | 25 |
| 7:1 | 80 | 2550 | 21 |
| 7:1 | 90 | 2560 | 19 |
| 7:1 | 100 | 2170 | 26 |
| 9:1 | 70 | 2480 | 20 |
| 9:1 | 80 | 2350 | 22 |
| 9:1 | 90 | 2300 | 21 |
| 9:1 | 100 | 2030 | 19 |

EXAMPLE 6

Preparation of High Viscosity Xanthan Using Dilution of Xanthan Broths Prior To Pasteurization A xanthan fermentation broth was diluted with various amounts of deionized water as shown in Table 6-1, then pasteurized as a function of temperature by pumping the diluted broths through heated tubes, prior to isopropyl alcohol precipitation. The recovered xanthan fibers were dried and milled into a powdered form. The recovered xanthan powders were rehydrated in synthetic tap water as in Example 3. The LSRV was measured as described in Example 1 and the results are presented in Table 6-1.

TABLE 6-1

Dilution ratios for water:xanthan broth with pasteurization temperatures and viscosity results.

| Dilution Ratio (water:broth) | Heating Temp. (° C.) | LSRV (cP) |
|---|---|---|
| 0:1 | none | 620 |
| 0:1 | 75 | 650 |
| 0:1 | 85 | 640 |
| 0:1 | 90 | 880 |
| 0:1 | 100 | 1290 |
| 0:1 | 110 | 1480 |
| 0:1 | 120 | 1340 |
| 0:1 | 130 | 1160 |
| 1:1 | 75 | 780 |
| 1:1 | 85 | 1520 |
| 1:1 | 90 | 1660 |
| 1:1 | 95 | 1710 |
| 1:1 | 105 | 1640 |
| 1:1 | 110 | 1490 |
| 1:1 | 115 | 1660 |
| 1:1 | 120 | 1600 |

TABLE 6-1-continued

Dilution ratios for water:xanthan broth with pasteurization temperatures and viscosity results.

| Dilution Ratio (water:broth) | Heating Temp. (° C.) | LSRV (cP) |
|---|---|---|
| 1:1 | 130 | 1490 |
| 2:1 | 90 | 2470 |

EXAMPLE 7

Preparation of High Viscosity Xanthan Using Different Diluents of Xanthan Broths Prior To Pasteurization A xanthan fermentation broth was divided into aliquots and diluted with 1.5 volumes of various diluents, including deionized water, tap water and soft water as shown in Table 7-1. The diluted broths are pasteurized at 90° C. for 5 minutes by passing the broths through heated coils, then cooled and precipitated into fibers with isopropyl alcohol. The xanthan fibers are oven dried and milled into powdered form. The recovered xanthan powders were rehydrated in synthetic tap water and seawater as in Example 3. The LSRV and SWV were measured as described in Examples 1 and 2, respectively and the results are set forth in Table 7-1. In addition, the relative ionic strengths of the diluted broths were determined by measuring their conductivities and are also set forth in Table 7-1.

TABLE 7-1

Dilution ratios for water:xanthan broth, pasteurization temperatures, viscosity results and conductivity results.

| Dilution Ratio (diluent:broth) | Diluent Type | LSRV (cP) | SWV (D. R.) | Conductivity (mmhos) |
|---|---|---|---|---|
| 0:1 | none | 900 | 15.5 | 5.68 |
| 1.5:1 | tap water | 1320 | 19.5 | 2.72 |
| 1.5:1 | soft water | 1570 | 22 | 2.42 |
| 1.5:1 | deionized water | 1710 | 22 | 2.40 |

EXAMPLE 8

Comparison of Xanthan Prepared Using Dilution of Xanthan Broth Prior To Pasteurization Versus Xanthan Prepared Using Ultrafiltration of Xanthan Broth Followed by Dilution and Pasteurization A xanthan fermentation broth was ultrafiltered until the volume of broth was 37% of its initial volume. The ultrafiltered broth was then diluted with deionized water to its initial volume. The diafiltered broth was pasteurized at 92° C. for five minutes by pumping the broths through a heated tube, then cooled to ambient temperature. A undiluted xanthan control was pasteurized at 92° C. and a deionized water diluted xanthan broth sample (1:1) was pasteurized at 92° C.

Xanthan was precipitated from each of the samples with isopropyl alcohol. The xanthan fibers are oven dried and milled into powdered form. The recovered xanthan powders were rehydrated in synthetic tap water and seawater as in Example 3. The LSRV and SWV were measured as described in Examples 1 and 2, respectively and the results are set forth in Table 8-1.

TABLE 8-1

Xanthan sample types, pasteurization temperatures and viscosity results.

| Xanthan Sample Type | Past. Temp. (° C.) | LSRV (cP) | SWV (D. R.) |
|---|---|---|---|
| undiluted control | 92 | 1034 | 18 |
| diafiltered | 92 | 1940 | 25 |
| 1:1 deionized water | 92 | 3085 | 28 |

EXAMPLE 9
Comparison of SWV and LSRV For High Viscosity Xanthan of the Present Invention To Commercial Xanthans LSRV and SWV values for a number of commercially available xanthans were determined using the processes described in Examples 1 and 2, respectively. The LSRV and SWV results for the commercial samples are set forth in Table 9-1 and are compared to the LSRV and SWV results for a xanthan using the disclosed dilution process of the present invention.

TABLE 9-1

LSRV and SWV values for commercially available xanthans compared to xanthan of the present invention.

| Sample | LSRV (cP) | SWV (D. R.) |
|---|---|---|
| Miles SD-1566 (Austria) | 1810 | 22.5 |
| Rhone Poulenc R-gel-200 (Courbevoie, France) | 1634 | 20 |
| Pfizer Flodril (New York, New York) | 1570 | 19.5 |
| Miles Jungbunzlauer 9708 (Austria) | 1710 | Not Determined |
| Rhone Poulenc Rhodigel CP-6092 (Courbevoie, France) | 1925 | Not Determined |
| World Fluids Xanthan-Ex (Cambridgeshire) | Not Determined | 25 |
| Archer Daniels Midland Flowzan GY95-358 (Decatur, IL) | 1500 | 20 |
| Example 5 Table 5-1 | 2500 | 28 |

EXAMPLE 10
Preparation of a High Viscosity Xanthan Using Direct Steam Injection Pasteurization With an In-Line Mixer of A Diluted Xanthan Fermentation Broth A xanthan recovery system was setup as illustrated in FIG. 1 with a QJET Heater setup as shown in FIG. 3 replacing the Silverson Machine Model 275L in-line mixer for pasteurization of the fermentation broth. Dilution of the product with steam condensate was estimated to be 8 weight percent. The direct steam injection apparatus was used to recovery a xanthan from a xanthan fermentation broth that had been diluted with deionized water prior to pasteurization. The xanthan had increased LSRV and SWV values compared to traditional pasteurization method used without dilution. The results for LSRV and SWV, the pasteurization method and the volume percentage dilution used is set forth in the following table.

TABLE 10-1

LSRV and SWV values for xanthans recovered from diluted xanthan broths pasteurized using a direct steam injection method and a plate heat exchanger method.

| | Pasteurization Method | SWV (D. R.) | LSRV (cP) | vol % Dilution With Deionized Water |
|---|---|---|---|---|
| Sample #1 | Direct Steam Injection | 28 | 2400 | 100 |
| Sample #2 | Direct Steam Injection | 25 | 2400 | 100 |
| Sample #3 | Direct Steam Injection | 24 | Not Determined | 100 |
| Sample #4 | Direct Steam Injection | 26 | 2200 | 150 |
| Sample #5 | Direct Steam Injection | 27 | Not Determined | 100 |
| Sample #6 | Plate Heat Exchanger | 22 | 2000 | 0 |

The direct steam injection process is capable of significantly improving the viscosity of a diluted xanthan fermentation broth. An additional advantage of the direct steam injection system is that examination of the system revealed that internal components were substantially clean and free of debris even after prolonged operating periods.

Other variations and modifications which will be obvious to those skilled in the art can be made in the foregoing examples without departing from the spirit or scope of the invention.

What is claimed is:

1. A xanthan gum having a sea water viscosity greater than 25 dial reading when dissolved in sea water to 0.29 weight percent.

2. The xanthan gum of claim 1, wherein said sea water viscosity is greater than 30 dial reading.

3. A xanthan gum having a low shear rate viscosity greater than 2000 cP when dissolved in synthetic tap water to 0.25 weight percent.

4. The xanthan gum of claim 3, wherein said low shear rate viscosity is greater than 3000 cP.

5. The xanthan gum of claim 3, wherein said xanthan gum is dissolved in sea water to 0.29 weight percent and has a sea water viscosity greater than 25 dial reading.

6. The xanthan gum of claim 5, wherein said xanthan gum is dissolved in sea water to 0.29 weight percent and has a sea water viscosity greater than 25 dial reading.

7. A xanthan gum having a sea water viscosity greater than 25 dial reading when dissolved in sea water to 0.29 weight percent prepared by the process comprising the steps of:
  (i) producing a xanthan gum in a fermentation broth by aerobic fermentation of a bacterium;
  (ii) diluting said fermentation broth with the sea water;
  (iii) pasteurizing said diluted fermentation broth using steam from a direct steam injection system to form the xanthan gum;
  (iv) cooling said pasteurized fermentation broth to an ambient temperature; and
  (v) precipitating said xanthan gum.

8. The xanthan gum of claim 7, wherein said bacterium is a *Xanthomonas bacterium*.

9. The xanthan gum of claim 8, wherein the *Xanthomonas bacterium* is selected from the group consisting of *Xanth-*

*omonas begoniae, Xanthomonas carotae, Xanthomonas campestris, Xanthomonas incanae, Xanthomonas phaseoli, Xanthomonas vesicatoria, Xanthomonas papavericola, Xanthomonas translucens, Xanthomonas vesicatoria*, and *Xanthomonas hedrae*.

10. The xanthan gum of claim 9, wherein the Xanthomonas bacterium is *Xanthomonas campestris*.

11. The xanthan gum of claim 7, wherein said xanthan gum has a sea water viscosity greater than 25 dial reading when dissolved in deionized water and wherein said process comprises the step of diluting said fermentation broth with deionized water.

12. The xanthan gum of claim 7, wherein said step of pasteurizing is conducted at a temperature from about 70° C. to about 120° C.

13. The xanthan gum of claim 12, wherein said temperature is from about 80° C. to about 110° C.

14. A xanthan gum having a low shear rate viscosity greater than 2000 cP when dissolved in synthetic tap water to 0.25 weight percent prepared by the process comprising the steps of:
   (i) producing a xanthan gum in a fermentation broth by aerobic fermentation of a bacterium;
   (ii) diluting said fermentation broth with synthetic tap water;
   (iii) pasteurizing said diluted fermentation broth using steam from a direct steam injection system to form the xanthan gum;
   (iv) cooling said pasteurized fermentation broth to an ambient temperature; and
   (v) precipitating said xanthan gum.

15. The xanthan gum of claim 14, wherein said bacterium is a Xanthomonas bacterium.

16. The xanthan gum of claim 15, wherein the *Xanthomonas* bacterium is selected from the group consisting of *Xanthomonas begoniae, Xanthomonas carotae, Xanthomonas campestris, Xanthomonas incanae, Xanthomonas phaseoli, Xanthomonas vesicatoria, Xanthomonas papavericola, Xanthomonas translucens, Xanthomonas vesicatoria*, and *Xanthomonas hedrae*.

17. The xanthan gum of claim 15, wherein the *Xanthomonas* bacterium is *Xanthomonas campestris*.

18. The xanthan gum of claim 14, wherein said xanthan gum has a low shear rate viscosity greater than 2000 cP when dissolved in deionized water and wherein said process comprises the step of diluting said fermentation broth with deionized water.

19. The xanthan gum of claim 14, wherein said step of pasteurizing is conducted at a temperature from about 70° C. to about 120° C.

20. The xanthan gum of claim 17, wherein said temperature is from about 80° C. to about 110° C.

21. The xanthan gum of claim 7, wherein said sea water viscosity is greater than 30 dial reading.

22. The xanthan gum of claim 14, wherein said low shear rate viscosity is greater than 3000 cP.

23. The xanthan gum of claim 14, wherein said xanthan gum is dissolved in sea water to 0.29 weight percent and has a sea water viscosity greater than 25 dial reading.

24. The xanthan gum of claim 23, wherein said xanthan gum is dissolved in sea water to 0.29 weight percent and has a sea water viscosity greater than 25 dial reading.

* * * * *

UNITED STATES PATENT AND TRADEMARK OFFICE
CERTIFICATE OF CORRECTION

PATENT NO. : 6,391,596 B1
DATED : May 21, 2002
INVENTOR(S) : Todd A. Talashek et al.

It is certified that error appears in the above-identified patent and that said Letters Patent is hereby corrected as shown below:

<u>Title page,</u>
Item [57], ABSTRACT,
Line 1, ""related" should read -- related to --; and
Line 10, "have" should read -- having --.

<u>Column 2,</u>
Line 34, "three fold" should read -- threefold --.

<u>Column 3,</u>
Line 47, "cause" should read -- causes --; and
Line 66, "cross" should read -- cross- --.

<u>Column 4,</u>
Lines 19 and 56, "have" should read -- having --.

<u>Column 5,</u>
Line 34, "elaborate a hydrophilic colloid" should be deleted; and
Line 39, "*Xanthomonas vesicatoria*," should be deleted.

<u>Column 6,</u>
Line 3, "50" should read -- 50 percent --; and
Line 62, "build up" should read -- buildup --.

<u>Column 8,</u>
Line 30, "an" should read -- a --.

<u>Column 9,</u>
Line 14, "allow" should read -- allowed --.

<u>Column 10,</u>
Line 45, "respectively" should read -- respectively, --.

<u>Column 11,</u>
Line 9, "respectively" should read -- respectively, --.

<u>Column 12,</u>
Lines 26 and 66, "respectively" should read -- respectively, --;
Line 51, "Pasteurization A" should read -- Pasteurization ¶A --; and
Line 58, "A" should read -- An --.

UNITED STATES PATENT AND TRADEMARK OFFICE
CERTIFICATE OF CORRECTION

PATENT NO. : 6,391,596 B1
DATED : May 21, 2002
INVENTOR(S) : Todd A. Talashek et al.

It is certified that error appears in the above-identified patent and that said Letters Patent is hereby corrected as shown below:

Column 13,
Line 55, "setup" should read -- set up --; and
Line 61, "recovery" should read -- recover --.

Column 14,
Line 47, "claim 5," should read -- claim 4, --.

Column 15,
Line 4, "*Xanthomonas vesicatoria*," should be deleted.

Column 16,
Line 8, "*Xanthomonas*" (second occurrence) should be deleted.
Line 9, "*vesicatoria*," should be deleted;
Line 9, "claim 15," should read -- claim 16, --; and
Line 19, "claim 17," should read -- claim 19, --.

Signed and Sealed this

Eighth Day of April, 2003

JAMES E. ROGAN
*Director of the United States Patent and Trademark Office*